(12) United States Patent
Wood

(10) Patent No.: US 11,547,844 B2
(45) Date of Patent: Jan. 10, 2023

(54) MULTI_USE DISINFECTING CAP AND METHOD

(71) Applicant: Barry Edward Wood, Georgiana, AL (US)

(72) Inventor: Barry Edward Wood, Georgiana, AL (US)

( * ) Notice: Subject to any disclaimer, the term of this patent is extended or adjusted under 35 U.S.C. 154(b) by 798 days.

(21) Appl. No.: 16/560,927

(22) Filed: Sep. 4, 2019

(65) Prior Publication Data

US 2020/0069932 A1 Mar. 5, 2020

Related U.S. Application Data

(60) Provisional application No. 62/727,266, filed on Sep. 5, 2018.

(51) Int. Cl.
| | | |
|---|---|---|
| *A61L 2/00* | (2006.01) | |
| *A61M 39/18* | (2006.01) | |
| *A61M 39/16* | (2006.01) | |
| *A61M 39/02* | (2006.01) | |
| *A61M 5/14* | (2006.01) | |
| *A01N 31/02* | (2006.01) | |
| *A61L 2/26* | (2006.01) | |
| *A61L 2/18* | (2006.01) | |
| *A01N 47/44* | (2006.01) | |
| *A61M 39/10* | (2006.01) | |

(52) U.S. Cl.
CPC ............ *A61M 39/18* (2013.01); *A01N 31/02* (2013.01); *A01N 47/44* (2013.01); *A61L 2/18* (2013.01); *A61L 2/26* (2013.01); *A61M 5/1413* (2013.01); *A61M 39/0208* (2013.01); *A61M 39/162* (2013.01); *A61M 39/165* (2013.01); *A61L 2202/122* (2013.01); *A61L 2202/24* (2013.01); *A61M 2039/1033* (2013.01); *A61M 2205/583* (2013.01)

(58) Field of Classification Search
CPC ........ A61L 2/00; A61L 2/18; A61L 2202/121; A61L 2202/122; A61L 2202/123; A61L 2202/24; A61M 39/18; A61M 39/165; A01N 47/44
USPC .......... 422/28, 292, 302; 604/283, 411, 905; 366/165, 264
See application file for complete search history.

(56) References Cited

U.S. PATENT DOCUMENTS

| | | | | |
|---|---|---|---|---|
| 5,190,534 A | * | 3/1993 | Kendell .................. | B08B 3/048 604/29 |
| 5,326,166 A | * | 7/1994 | Walthall .................. | B01F 25/10 239/10 |

* cited by examiner

*Primary Examiner* — Monzer R Chorbaji
(74) *Attorney, Agent, or Firm* — Sandra L. Layer

(57) ABSTRACT

A multi-use disinfecting cap and method for disinfection and protection of a needleless IV injection port. The disinfecting cap has an upper chamber which contains a sterilizing solution and a low chamber which connects to a needleless IV injection port. The fluid can be manipulated to flow between the two chambers. When in use the cap protects and disinfects a needleless IV injection port when exposed prior to injecting medication into the needleless port and continues to disinfect and protect prior for any subsequent exposures. The cap is re-usable and provides a clear indication of the disinfecting solution and a datable top surface. The multi-use disinfecting cap may be removably clipped to the IV tubing and is shaped to prevent accidental rolling away if dropped.

8 Claims, 4 Drawing Sheets

MULTI_USE DISINFECTING CAP AND METHOD

BACKGROUND OF THE INVENTION

Related Application

The present patent application claims priority to the corresponding provisional patent application Ser. No. 62/727,266, entitled "MULTI-USE DISINFECTING CAP" filed on Sep. 5, 2018.

Field of the Invention

The present invention relates to a multi-use disinfecting cap and method and more particularly pertains to a multi-use cap for disinfection and protection of a needleless IV injection port and method of use.

Description of the Prior Art

The use of disinfecting caps is known in the prior art. More specifically, disinfecting caps previously devised and utilized for the purpose of disinfecting the surface of a needleless IV injection port are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, the aforementioned patents do not describe multi-use disinfecting cap and method that allows a multi-use cap for disinfection and protection of a needleless IV injection port and method of use.

In this respect, the multi-use disinfecting cap and method according to the present invention substantially departs from the conventional concepts and designs of the prior art, and in doing so provides an apparatus primarily developed for the purpose of a multi-use cap for disinfection and protection of a needleless IV injection port and method of use.

Therefore, it can be appreciated that there exists a continuing need for a new and improved multi-use disinfecting cap and method which can be used for a multi-use cap for disinfection and protection of a needleless IV injection port and method of use. In this regard, the present invention substantially fulfills this need.

SUMMARY OF THE INVENTION

In view of the foregoing disadvantages inherent in the known types of disinfecting caps now present in the prior art, the present invention provides an improved multi-use disinfecting cap and method. As such, the general purpose of the present invention, which will be described subsequently in greater detail, is to provide a new and improved multi-use disinfecting cap and method which has all the advantages of the prior art and none of the disadvantages.

To attain this, for a broad perspective, the present invention essentially comprises a disinfecting cap having an upper chamber and a lower chamber. The upper chamber having an upper cylindrical section. The top of the upper cylindrical section sealed with a planar surface. The upper chamber having a lower conical section forming a funnel and in fluid communication with the lower chamber. The upper chamber being transparent to view the tinted disinfecting solution contained in the upper chamber. The lower chamber being transparent to view the tinted disinfecting solution when present in the lower chamber. The lower chamber being cylindrical having an upper end formed with an annular ridge projecting radially inward in proximity to the lower conical section of the upper chamber. The lower chamber having an interior surface formed with female threads. The lower extent of the lower chamber adapted to receive a needleless IV connector port. The lower chamber having an open lower end. A removable seal covering the open lower end of the lower chamber.

One optional feature of the disinfecting cap is a broadened annular flange to increase the size of the upper planar surface for accepting indicia and sealing the top.

Another optional feature is a slot formed in the outer edge of the annular flange to connect the disinfecting cap to an IV line constricting the line and for handling purposes to keep the cap close.

An additional optional feature is a sponge contained in the lower chamber to facilitate movement of the disinfecting solution between the upper chamber and a connected needleless IV port.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved multi-use disinfecting cap which has all of the advantages of the prior art disinfecting caps and none of the disadvantages.

It is another object of the present invention to provide a new and improved multi-use disinfecting cap which may be easily and efficiently manufactured and marketed.

It is a further object of the present invention to provide a new and improved multi-use disinfecting cap which is of durable and reliable constructions.

An even further object of the present invention is to provide a new and improved multi-use disinfecting cap which is susceptible of a low cost of manufacture with regard to both materials and labor, and which accordingly is then susceptible of low prices of sale to the consuming public, thereby making such multi-use disinfecting cap economically available to the buying public.

Lastly, it is an object of the present invention to provide a multi-use disinfecting cap for safe multiple use protection and disinfecting of needleless IV ports before, between and after exposures of the needless IV connecting port for injections of medicine.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
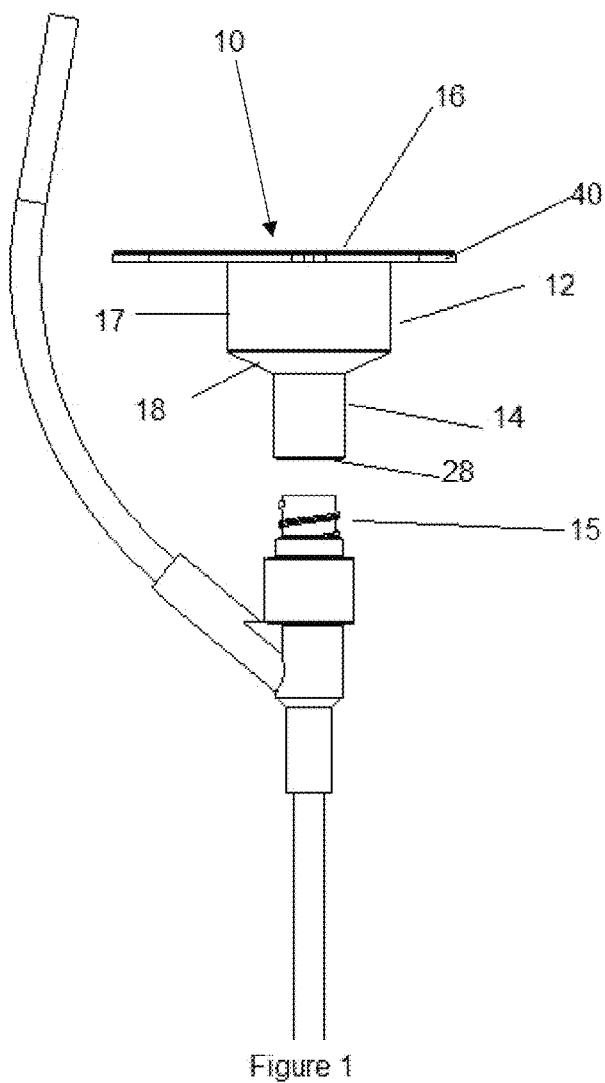
FIG. 1 is a front perspective view of a disinfecting cap constructed in accordance with the principles of the present invention shown as used for connecting to a needleless IV port.

With reference now to the drawings, and in particular to FIG. 1 thereof, the preferred embodiment of the new and improved multi-use disinfecting cap and method embodying the principles and concepts of the present invention and generally designated by the reference numeral 10 will be described.

The present invention, the multi-use disinfecting cap 10 is comprised of a plurality of components. Such components are individually configured and correlated with respect to each other so as to attain the desired objective. In their broadest context such include an upper chamber and a lower chamber. The upper chamber transparent and in fluid communication with the lower chamber. The top of the upper chamber sealed with a planar surface. The upper chamber is filled with tinted disinfecting solution, such as isopropyl alcohol or chlorhexidine. The transparent lower chamber is configured to couple to a needleless IV port connector. In this broad context, first provided is an upper chamber 12 and a lower chamber 14. The upper chamber 12 sealed on top with a planar surface 16 capable of receiving indicia and in fluid communication with the lower chamber 14. A tinted disinfecting solution is contained in the upper chamber. Both the upper and lower chambers are transparent. The lower chamber having an upper end with one or more annular ridges projecting inward in proximity to the conical section 18 of the upper chamber. The lower extent of the lower chamber is adapted to receive a needleless IV connector port 15. The lower chamber having an open lower end and a removable seal 28 covering the open end 26 of the lower chamber. Such components are individually configured and correlated with respect to each other so as to attain the desired objective.

In the preferred embodiment of the multi-use disinfecting cap, designated by reference numeral 10 and shown in FIGS. 1-5, first provided is a disinfecting cap configured for use with a needless IV port. The cap comprising an upper chamber 12 and a lower chamber 14. The upper chamber having a closed top and an open lower end. The top of the upper chamber is sealed with an upper seal consisting of a planar surface 16 for receiving written indicia. The upper chamber 12 being transparent. The upper chamber having an upper cylindrical section 17 with a diameter of 0.83 inches plus or minus 10 percent. The upper chamber having a lower conical section 18 forming a funnel in fluid communication with the lower chamber with an axial opening 24 on the lower end. The upper chamber is filled with tinted disinfecting solution, the tinted disinfecting solution taken from a class of disinfectants including isopropyl alcohol and chlorhexidine.

Figure 2:
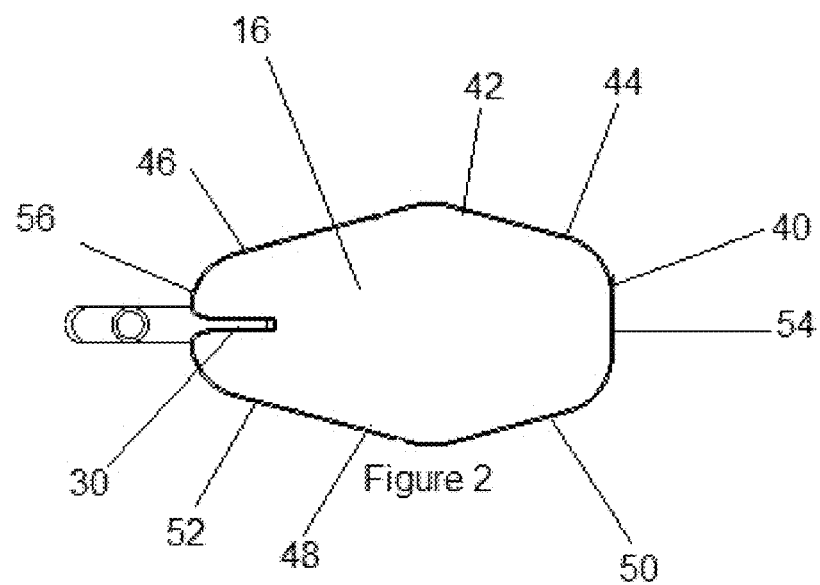
FIG. 2 is a top view of an alternate embodiment of a disinfecting cap constructed in accordance with the principles of the present invention and having a slot for connecting to an IV tube.
Figure 3:
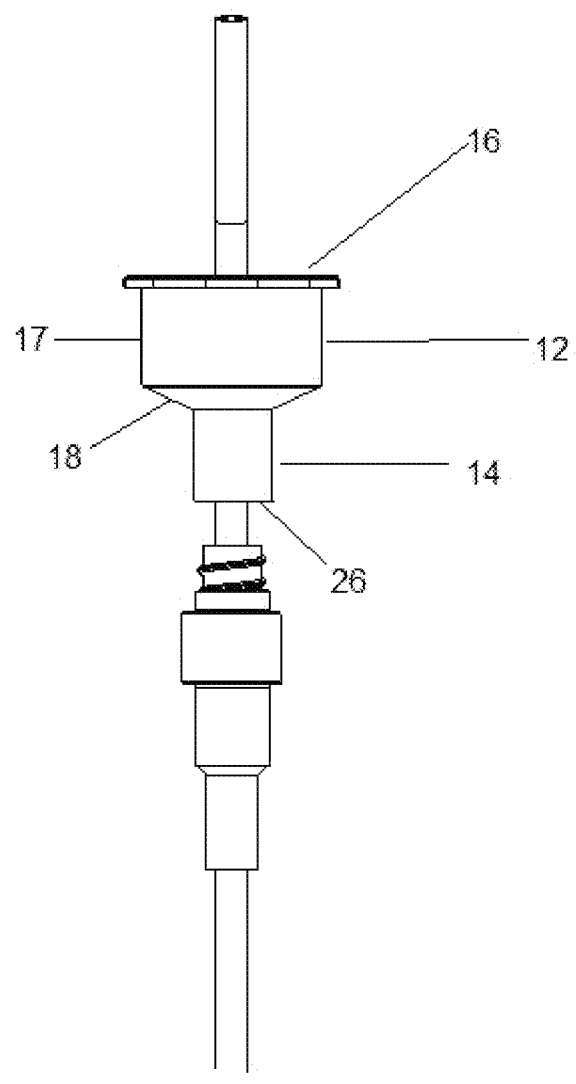
FIG. 3 is a side perspective view of a disinfecting cap constructed in accordance with the principles of the present invention shown as used for connecting to a needleless IV port.
Figure 4:
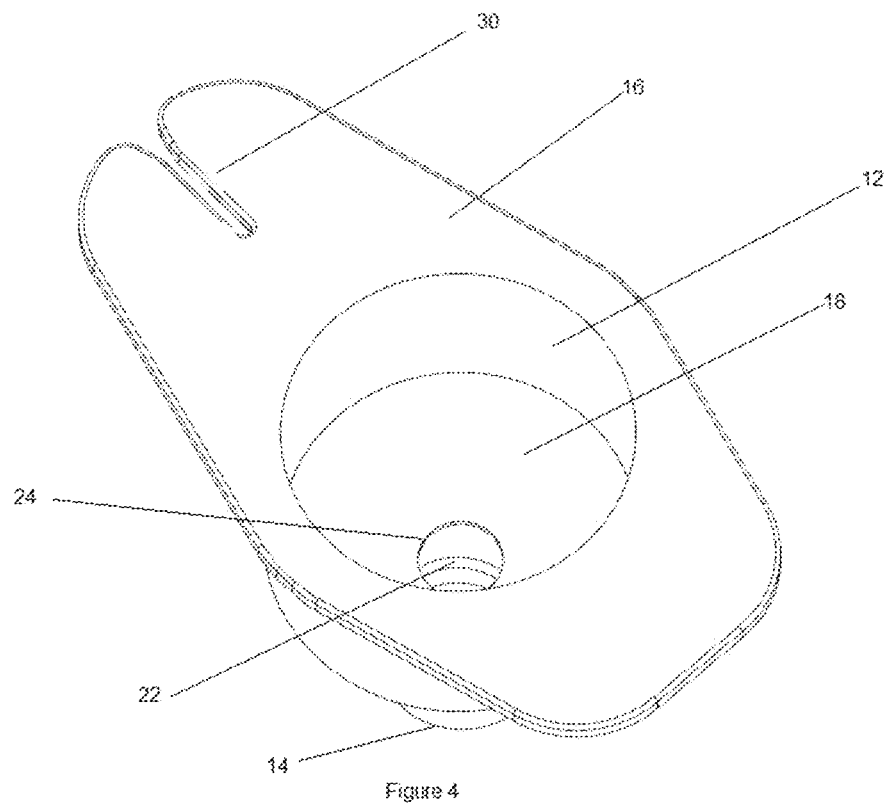
FIG. 4 is a top perspective view of a disinfecting cap constructed in accordance with the principles of the present invention shown as used for connecting to a needleless IV port.
Figure 5:
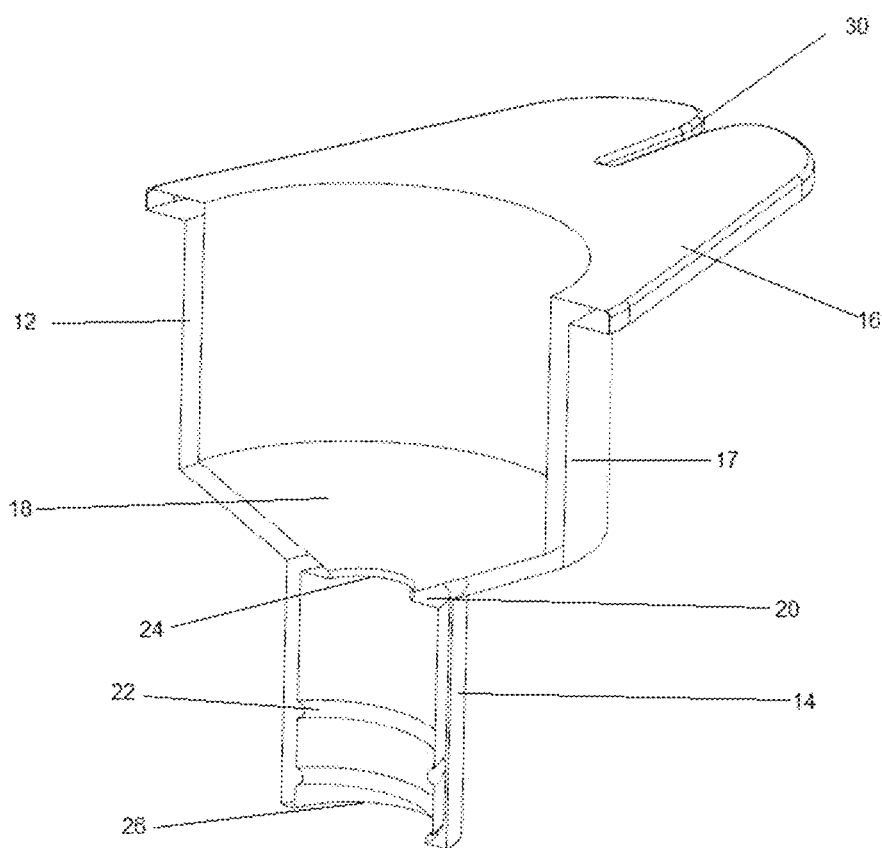
FIG. 5 is a cross-sectional view of a disinfecting cap constructed in accordance with the principles of the present invention.

The lower chamber 14 is below and in fluid connection with the upper chamber. The lower chamber 14 is cylindrical and transparent. The lower chamber having a second diameter of 0.36 inches plus or minus 10 percent and a height of 0.425 inches plus or minus 10 percent. The lower chamber is formed with an annular ridge 20 (shown in FIG. 5) projecting inward in proximity to the lower conical section 18 of the upper chamber. The lower extent of the lower chamber having female threads 22 (shown in FIG. 5) adapted to receive a needleless IV connector port 15 such as a female luer connector port. The lower chamber is in fluid connection with the top of the needleless IV connector port 15 (needleless IV connector port in the form of a female luer connecter port is shown in FIGS. 1, 2 and 3 for reference only) when coupled. A removable seal 28 covers the lower edge 26 of the lower chamber.

The removable seal 28 of the lower edge is removable for use before removably connecting to the needleless IV connector port 15 allowing disinfecting fluid to contact the upper surface of the needleless IV connector port.

In one alternate embodiment, an annular flange 40 (shown in FIGS. 2, 4 and 5) extends radially outward from the top of the upper cylindrical section forming an enlarged planar surface for connecting the upper seal and increasing the planar writing surface. The flange is formed in a planar configuration having a first side edge 42 with a central bend forming an obtuse angle. The first side edge has an interior end 44 and an exterior end 46. The flange has a second side edge 48 with a central bend forming an obtuse angle. The second side edge having an interior end 50 and an exterior end 52. A first end edge 54 in a linear configuration couples the interior end 44 of the first side edge 42 and the interior end 50 of the second side edge 48 and a second end edge 56 in an arcuate configuration couples the exterior end of the first side edge 56 with the exterior end of the second side edge 52.

In still another embodiment a radial slot 30 (shown in FIGS. 2, 4, and 5) is cut into the flange for attaching to and constricting the IV tube when disconnecting the disinfecting cap to access the needleless IV port.

Figure 6:
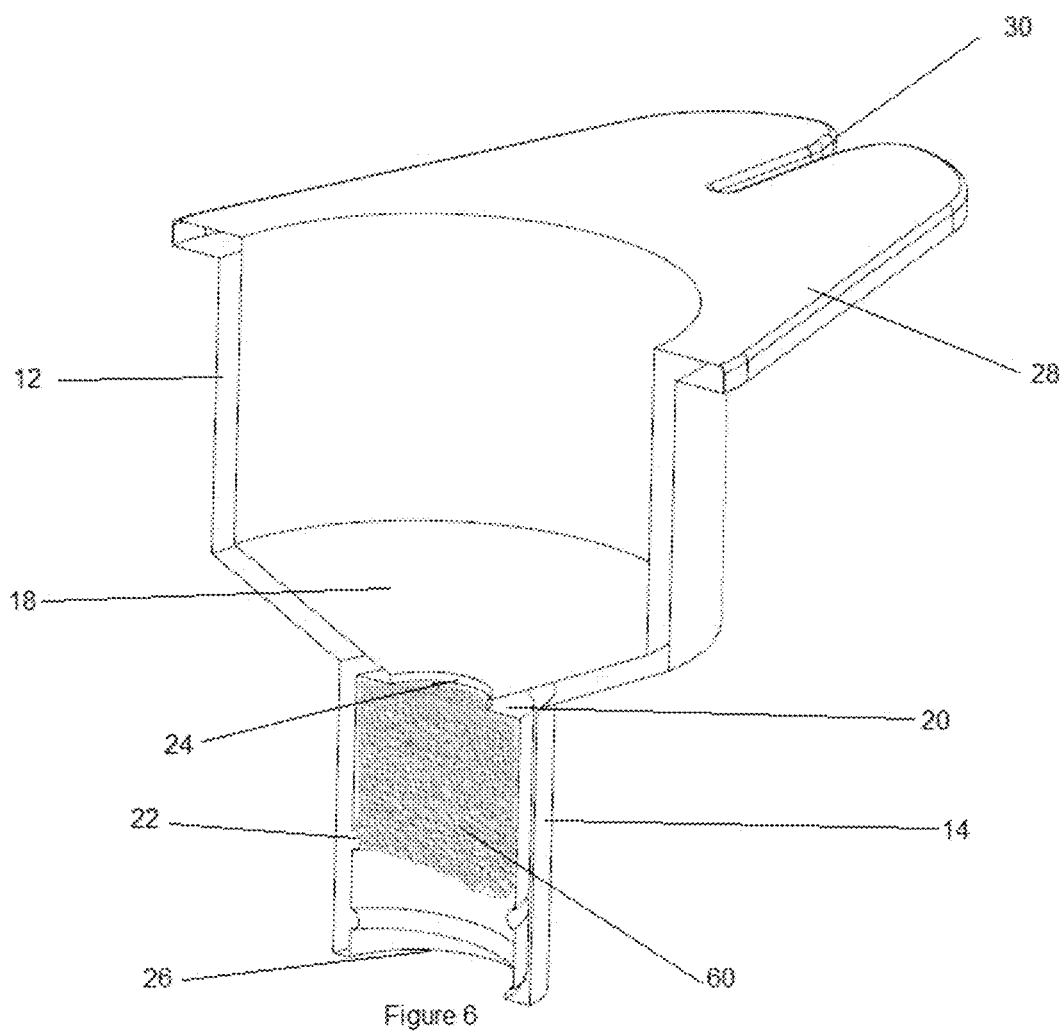
FIG. 6 is a cross-sectional view of a disinfection cap constructed in accordance with the principles of an alternate embodiment of the present invention including a sponge in the lower chamber.

In still another alternate embodiment (shown in FIG. 6) a sponge 60 is located in the lower chamber to facilitate movement of the disinfecting solution from the upper chamber to the top of the needleless IV injection port.

A method of use is also provided, the method comprising the steps as follows:

a. Providing a disinfecting cap having an upper chamber and a lower chamber. The upper chamber sealed on top with a planar surface capable of receiving indicia and in fluid communication with the lower chamber. A tinted disinfecting solution is contained in the upper chamber. Both the upper and lower chambers are transparent. The lower chamber having an upper end with one or more ridges projecting inward in proximity to the conical section of the upper chamber. The lower extent of the lower chamber is adapted to receive a needleless IV connector port. The lower chamber having an open lower end and a removable seal covering the open end of the lower chamber.

b. Writing the date and time on the planar surface on top of the upper chamber.

c. Removing the lower seal from the lower chamber.

d. Securing the lower chamber to a needleless IV injection port.

e. Shaking the disinfecting cap to the force disinfecting solution to flow from the upper chamber to the lower chamber adjacent to the top of the needleless IV injection port.

f. Waiting for the disinfecting solution to disinfect the top of the needleless IV injection port (as required by the specific solution, usually a minimum of 15 seconds).

g. Removing the disinfecting cap from needleless IV injection port.

h. Connecting the disinfecting cap to a piece of IV tubing by pushing the tubing into the small slot eliminating the need to use the IV tubing roller clamp for preventing back-flow while injecting medication into the port.

i. Injecting medication as needed into the needless port.

j. Disconnecting the disinfecting cap from the IV tubing by removing the tubing from the slot.

k. Securing the lower chamber to the needleless injection port.

l. Shaking the disinfecting cap to force disinfecting solution to flow from the upper chamber to the lower chamber to disinfect the port for subsequent injections.

The cap is a multiuse cap for disinfecting and protecting a needless IV injection port. The transparent chambers and tinted disinfecting solution allow for multiple use by providing a visual indication of useful solution. The cap is a small dual chambered device comprised of a larger chamber that acts as a reservoir and a smaller chamber that acts to keep alcohol in contact with the needleless IV port. The surface tension of the solution and the vacuum created once the device is secured to the port keeps the solution in contact with the port. A small annular ridge separates the two chambers and prevents the smaller volume from flowing back into the larger chamber if the device is turned upside down. The larger chamber is tapered to facilitate flow into the smaller chamber. Once the solution flows into the smaller chamber it will remain in contact with the top of the needleless IV injection port (luer valve) thus sterilizing the port. The seal on the top of the larger upper chamber may be written on to allow for dating when first connected to the IV tubing. The seal on the bottom of the smaller lower chamber is removable to provide access to the solution when connected to the needleless IV injection port (luer valve). The visibility of the tinted solution within the chambers allows nurses and practitioners to easily see that the disinfecting solution is in contact with the port prior to removing for access and reconnecting following injection making the cap ideal for multiuse. The small slot in the top of the cap can be used to secure the cap to the IV tubing both to prevent loss and to eliminate the need for a separate IV tubing roller clamp for preventing back-flow while injecting medication into the exposed port. The angular oval shape of the top flange also prevents rolling in the event the cap is dropped. All of these features result in a device that enhances workflow rather than impeding it. As a nurse anesthetist I constantly access the port during a case. Other devices require constant replacement in order to maintain the proper level of disinfection. In addition to clear indication of the disinfecting solution and datable aging this cap has additional feature to keep it close by clipping to the IV tubing and being shaped to prevent accidental rolling away.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A disinfecting cap, the disinfecting cap having an upper chamber and a lower chamber, the upper chamber having an upper cylindrical section, the upper cylindrical section having a top, the top of the upper cylindrical section sealed with a planar surface, the upper chamber having a lower conical section, the lower conical section forming a funnel, the lower conical section in fluid communication with the lower chamber, the upper chamber being transparent, a tinted disinfecting solution contained in the upper chamber, the lower chamber being transparent, the lower chamber being cylindrical, the lower chamber having an upper end, the lower chamber having an annular ridge projecting radially inward in proximity to the lower conical section of the upper chamber, the lower chamber having an interior surface, the interior surface of the lower extent of the lower chamber being formed with female threads, the lower extent of the lower chamber adapted to receive a needleless IV connector port, the lower chamber having a lower end, the lower end of the lower chamber being open, a removable seal covering the open end of the lower end of the lower chamber.

2. The disinfecting cap of claim 1 wherein the tinted disinfecting solution is taken from a class of disinfecting solutions including isopropyl alcohol and chlorhexidine.

3. The disinfecting cap of claim 1 in which the top of the upper cylindrical section is formed with a flange extending radially outward forming an enlarged planar surface, the flange in a planar configuration having a first side edge with a central bend forming an obtuse angle, the first side edge having an interior end and an exterior end, the flange having a second side edge with a central bend forming an obtuse angle, the second side edge having an interior end and an exterior end, a first end edge in a linear configuration coupling the interior end of the first side edge and the interior end of the second side edge, a second end edge in an arcuate configuration coupling the exterior end of the first side edge with the exterior end of the second side edge.

4. The disinfecting cap of claim 3 further including a radial slot formed centrally in the second end edge.

5. The disinfecting cap of claim 1 wherein the upper planar surface is capable of receiving indicia.

6. The disinfecting cap of claim 1 further comprising a sponge contained in the lower chamber.

7. A disinfecting cap configured for use for use with a needleless IV port, the disinfecting cap comprising an upper chamber and a lower chamber, the upper chamber having an upper cylindrical section, the upper cylindrical section having a top, the top of the upper cylindrical section sealed, the top of the upper cylindrical section formed with a flange extending radially outward forming an enlarged planar surface, the flange in a planar configuration having a first side edge with a central bend forming an obtuse angle, the first side edge having an interior end and an exterior end, the flange having a second side edge with a central bend forming an obtuse angle, the second side edge having an interior end and an exterior end, a first end edge in a linear configuration coupling the interior end of the first side edge and the interior end of the second side edge, a second end edge in an arcuate configuration coupling the exterior end of the first side edge with the exterior end of the second side edge, a radial slot formed centrally in the second end edge;

the upper chamber having a lower conical section, the lower conical section forming a funnel, the lower conical section in fluid communication with the lower chamber, the upper chamber being transparent, the upper chamber filled with a tinted disinfecting solution, the tinted disinfecting solution taken from a class of disinfecting solutions including isopropyl alcohol and chlorhexidine;

the lower chamber below and in fluid connection with the upper chamber, the lower chamber being cylindrical, the lower chamber being transparent, the lower chamber having an upper extent and a lower extent, the lower chamber having an annular ridge projecting radially inward in proximity to the lower conical section of the upper chamber, the lower chamber having an interior surface, the interior surface of the lower extent of the lower chamber being formed with female threads, the lower extent of the lower chamber adapted to receive a needleless IV connector port, the lower chamber having a lower end, the lower end of the lower chamber being open, a removable seal covering the open end of the lower end of the lower chamber, the lower chamber having an upper edge and a lower edge; and the removable seal of the lower edge removable for use before removably coupling to the needleless IV connecter port, the lower chamber in fluid connection with the top of the needleless IV connecter port when coupled allowing disinfecting fluid to contact the top of the needleless IV connecter port.

8. A method for disinfecting, protecting and maintaining a needleless IV port, the method comprising the steps of:

providing a disinfecting cap, the disinfecting cap having an upper chamber and a lower chamber, the upper chamber having an upper cylindrical section, the upper cylindrical section having a top, the top of the upper cylindrical section sealed with a planar surface capable of receiving indicia, the top of the upper cylindrical section is formed with an annular flange extending outward from the upper edge forming an enlarged planar surface, a slot extending inward from the external circumference of the enlarged planar surface, the upper chamber having a lower conical section, the lower conical section forming a funnel, the lower conical section in fluid communication with the lower chamber, the upper chamber being transparent, tinted disinfecting solution contained in the upper chamber, the lower chamber being transparent, the lower chamber being cylindrical, the lower chamber having an upper end, the lower chamber having an annular ridge projecting radially inward in proximity to the lower conical section of the upper chamber, the interior of the lower extent of the lower chamber being internally threaded, the lower extent of the lower chamber adapted to receive a needleless IV connector port, the lower chamber having a lower end, the lower end of the lower chamber being open, a removable seal covering the open end of the lower end of the lower chamber;

writing the date and time on upper surface of the upper chamber;

removing the lower seal from lower chamber;

coupling the lower chamber to a needleless IV injection port;

shaking the disinfecting cap to force disinfecting solution to flow from the upper chamber to the lower chamber;

waiting for the disinfecting solution to disinfect the top of the needleless IV injection port;

removing the disinfecting cap from the needleless injection port;

connecting the disinfecting cap to a piece of IV tubing attached to the needleless IV port by pushing the IV tubing into the small slot constricting the IV tubing;

injecting medication as needed into the needless port;

disconnecting the cap from the IV tubing by removing the IV tubing from the slot;

coupling the lower chamber to the needleless IV injection port;

shaking the disinfecting cap to force disinfecting solution to flow from the upper chamber to the lower chamber, disinfecting the top of the needleless IV injection port for subsequent injections.

* * * * *